(12) United States Patent
Enomoto et al.

(10) Patent No.: US 9,417,228 B2
(45) Date of Patent: Aug. 16, 2016

(54) METHOD OF PREDICTING VISCOSITY BEHAVIOR OF THERMOSETTING RESIN, SIMULATION SOFTWARE, METHOD OF PRODUCING THERMOSETTING RESIN, AND UNDERFILL PRODUCED IN THE PRODUCTION METHOD

(71) Applicant: Namics Corporation, Nigata (JP)

(72) Inventors: Toshiaki Enomoto, Niigata (JP); Arata Hayashigaki, Tokyo (JP); Masaaki Hoshiyama, Niigata (JP); Toyokazu Hotchi, Niigata (JP); Toshiyuki Sato, Niigata (JP)

(73) Assignee: Namics Corporation, Niigata (JP)

( * ) Notice: Subject to any disclaimer, the term of this patent is extended or adjusted under 35 U.S.C. 154(b) by 23 days.

(21) Appl. No.: 14/256,201

(22) Filed: Apr. 18, 2014

(65) Prior Publication Data
US 2014/0316102 A1 Oct. 23, 2014

(30) Foreign Application Priority Data
Apr. 18, 2013 (JP) ................................. 2013-087759

(51) Int. Cl.
*G01N 33/44* (2006.01)
*G01N 11/00* (2006.01)
*C09J 9/00* (2006.01)

(52) U.S. Cl.
CPC .............. *G01N 33/442* (2013.01); *G01N 11/00* (2013.01); *G01N 2011/0093* (2013.01); *H01L 2224/16225* (2013.01); *H01L 2224/32225* (2013.01); *H01L 2224/73204* (2013.01); *H01L 2224/92125* (2013.01)

(58) Field of Classification Search
CPC .......................................................... G01N 33/44
USPC ................................. 528/421; 436/2; 702/50
See application file for complete search history.

(56) References Cited

FOREIGN PATENT DOCUMENTS

JP 08-15119 A 1/1996

*Primary Examiner* — Duc Truong
(74) *Attorney, Agent, or Firm* — Westman, Champlin & Koehler, P.A.

(57) ABSTRACT

A method of predicting viscosity behavior of a thermosetting resin is provided that is capable of predicting viscosity behavior of a thermosetting resin and void generation in the underfill is suppressed while good solder connection is obtained. The method includes: measuring a reaction rate and measuring viscosity behavior to measure a calorimetry peak and viscosity behavior of the thermosetting resin with three or more rates of temperature increase respectively; fitting a reaction rate to fit measurement data with each rate of temperature increase obtained by the measuring a reaction rate to a Kamal model formula to obtain fitting curves; fitting viscosity behavior to fit parameters in the Kamal model formula and the measurement data for each rate of temperature increase obtained by the measuring viscosity behavior to a Castro-Macosko model formula to obtain fitting curves; and calculating virtual viscosity behavior to calculate virtual viscosity behavior of the thermosetting resin at the arbitrary rate of temperature increase by simulation based on each fitting curve for each rate of temperature increase obtained by the fitting viscosity behavior.

8 Claims, 13 Drawing Sheets

Fig. 5
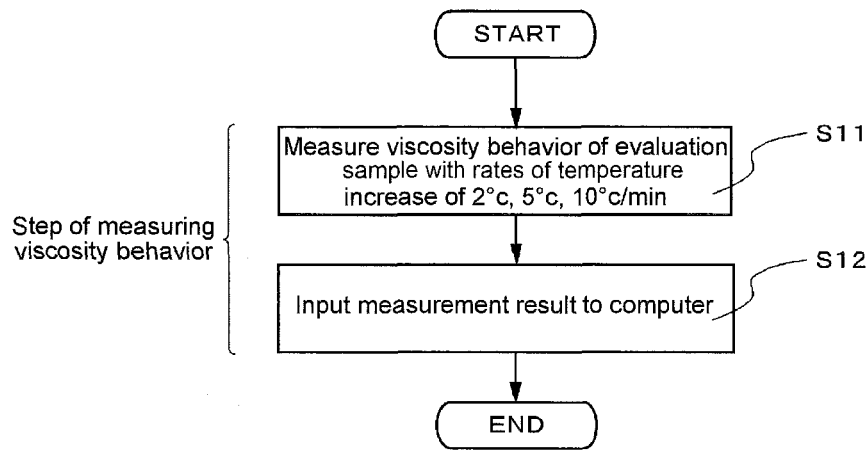
Fig. 6A
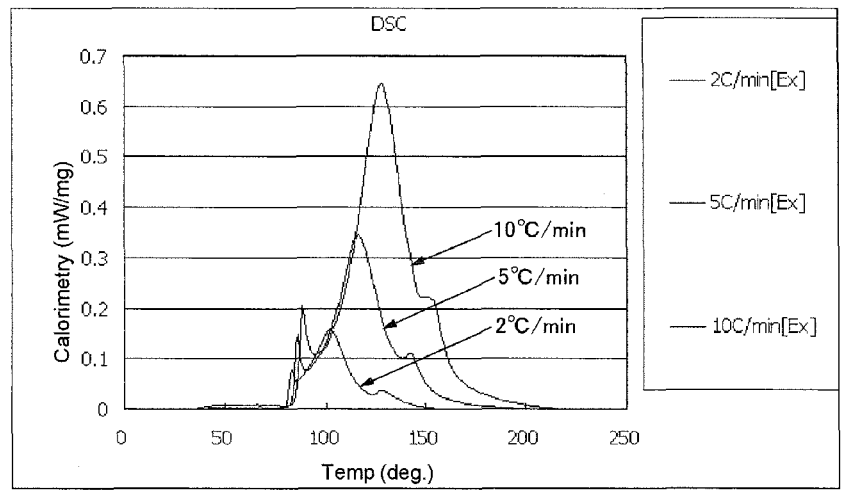
Reaction rate measurement result
Fig. 6B
|  | Calorimetry (mW/mg) | Ratio to average |
|---|---|---|
| 2°C/min | 127.1 | 92% |
| 5°C/min | 142.5 | 103% |
| 10°C/min | 145.9 | 105% |
| average | 138.5 |  |
Gross calorific value for each rate of temperature increase Measurement result of temperature dependent viscosity Fig. 9A
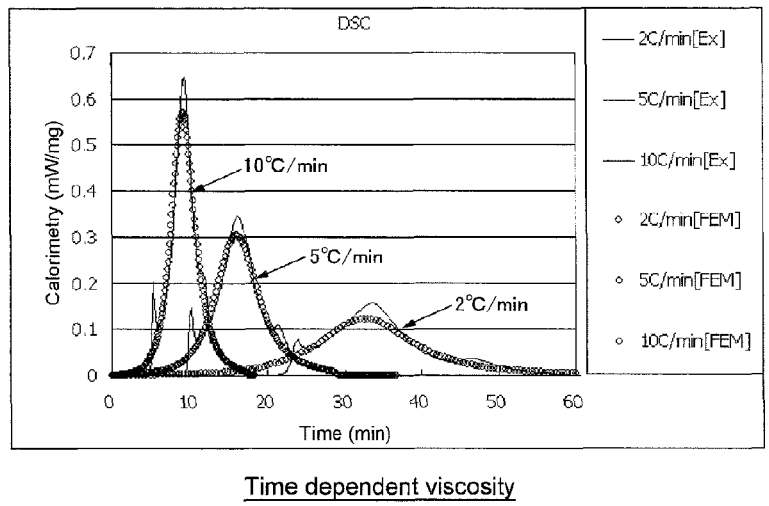
Time dependent viscosity
Fig. 9B
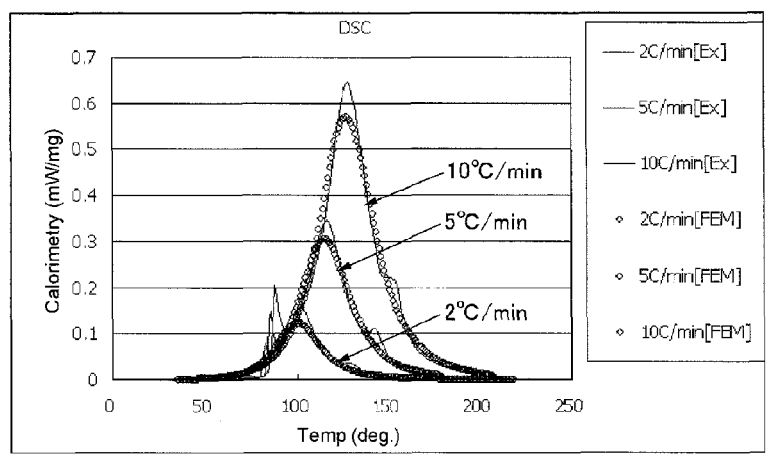
Temperature dependent viscosity
Fig. 10
| Kamal model | input data |
|---|---|
| A1 | 8.12E+09 |
| A2 | 1.32E+08 |
| E1 | 9.33E+03 |
| E2 | 2.38E+03 |
| m | 9.80E-01 |
| n | 2.00E+00 |
| B1 | 2.50E+09 |
| B2 | 1.00E+05 |
| F1 | 1.89E+09 |
| F2 | 0.00E+00 |
| p | 1.14E+03 |
| q | 2.53E+04 |
| Tb | 2.01E+02 |
| T0 | 2.73E+02 |
List of parameters by reaction rate fitting Fig. 11A
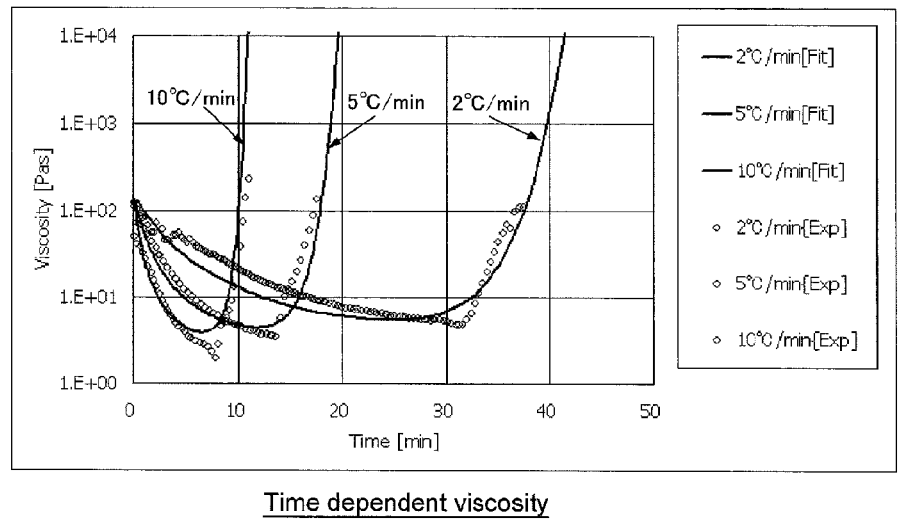
Time dependent viscosity
Fig. 11B
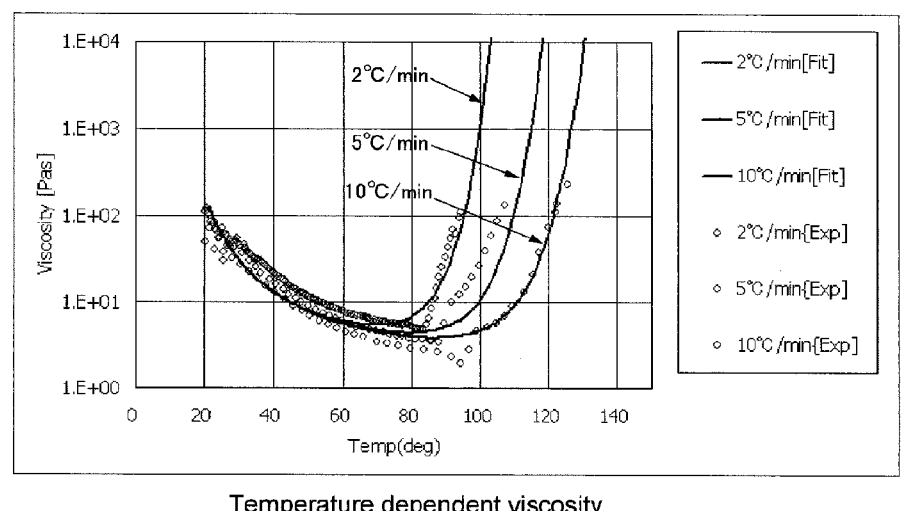
Temperature dependent viscosity
Fig. 12
| Cross-Macosko model | input data |
|---|---|
| B | 1.71E+01 |
| TB | 1.13E+02 |
| tau* | 1.00E-10 |
| r | 9.00E-01 |
| omega[1/s] | 6.28E+00 |
| agel | 9.00E-01 |
| E | 6.12E+00 |
| F | 4.41E+00 |
List of parameters by viscosity behavior fitting Time dependent viscosity Temperature dependent viscosity Temperature dependent viscosity prediction result Dispense
Flux Mounting Reflow Flux cleaning Dispense Curing Dispense Bonding Post cure

METHOD OF PREDICTING VISCOSITY BEHAVIOR OF THERMOSETTING RESIN, SIMULATION SOFTWARE, METHOD OF PRODUCING THERMOSETTING RESIN, AND UNDERFILL PRODUCED IN THE PRODUCTION METHOD

TECHNICAL FIELD

The present invention relates to a method of predicting viscosity behavior of a thermosetting resin, simulation software, a method of producing a thermosetting resin, and underfill produced in the production method in order to predict viscosity behavior of a thermosetting resin with an arbitrary rate of temperature increase. More specifically, the present invention relates to a method of predicting viscosity behavior of a thermosetting resin, simulation software, a method of producing a thermosetting resin, and underfill produced in the production method in which viscosity behavior of a thermosetting resin, when a thermal compression bonding technique (TCB) is carried out, may be predicted, and void generation in the underfill is suppressed while good solder connection is obtained.

BACKGROUND ART

Conventionally, there is a known capillary flow technique using capillary underfill (CUF) illustrated in FIGS. 17A to 17F as a flipchip mounting method. In the capillary flow technique, firstly flux is applied on a substrate terminal (FIG. 17A), and subsequently an IC chip provided with a solder ball is placed on the flux (FIG. 17B), followed by performing reflow soldering (FIG. 17C). After that, excess flux is cleaned (FIG. 17D) and the underfill is poured into a gap between the chip and the substrate utilizing a capillary phenomenon (FIG. 17E), and the underfill is thermoset by heat treatment (FIG. 17F).

However, in such capillary flow technique, use of flux, other than the underfill, is essential and also the steps of applying the flux (FIG. 17A) and cleaning the flux (FIG. 17D) have to be carried out, so that it was not possible to efficiently mount an IC chip. Particularly, in the cleaning step (FIG. 17D), it was sometimes not possible to wash away excess flux thoroughly.

With that, as a flipchip mounting method without using flux, there is a thermal compression bonding (TCB) technique using a preapplied underfill material (PAM) as illustrated in FIGS. 18A to 18C. In this technique, firstly, underfill of a preapplied type, such as non-conductive paste (NCP), for example, is applied on a substrate terminal (FIG. 18A), and subsequently, an IC chip provided with a solder ball is thermocompression bonded on the underfill (FIG. 18B). Due to the thermocompression bonding, the solder ball of the IC chip is melted and also the underfill is primarily cured. After that, the underfill is post cured by heat treatment (FIG. 18C).

Such thermal compression bonding technique takes not more than three steps, which are the step of applying underfill, the step of thermocompression bonding an IC chip and the step of heat treatment without using flux. Therefore, it is possible to efficiently mount an IC chip with the technique.

An example of the related technique may be found in JP H8-15119 A.

DISCLOSURE OF THE INVENTION

However, the above thermal compression bonding technique used to have a problem that, in the step of thermocompression bonding an IC chip illustrated in FIG. 18B, it was difficult to manage both suppression of void formation in the underfill and good solder connection.

That is, in the step of thermocompression bonding an IC chip illustrated in FIG. 18B, when the viscosity of the primarily cured underfill is too low, it is not possible to suppress generation of outgas, which is liable to create voids. Therefore, in the step of thermocompression bonding an IC chip, whether or not outgas is generated is determined by the magnitude of the viscosity of the underfill. When outgas is generated, it turns out to create voids.

On the other hand, in the step of thermocompression bonding an IC chip illustrated in FIG. 18B, when the viscosity of the underfill is too high, the connection between the solder ball and the substrate terminal is blocked by the underfill. It is desirable that the underfill exhibits viscosity behavior in which thickening does not start until the melted solder is wet spread. When the underfill first starts thickening before the solder is wet spread, the solder wet spread is blocked and thus contact failure occurs.

Currently, as a condition required for non-conductive paste, for example, with a condition of a mounting tact of 4 sec, the rate of temperature increase goes up to 260° C. at 1800° C./min (approximately 30° C./sec) whereas voids occur in the composition of non-conductive paste in the current state. For suppression of void formation, it is considered to be advantageous that the resin is highly viscous at a solder melting temperature of around 220° C. However, in conventional methods, the viscosity behavior has to be predicted based on temperature dependent viscosity data in which non-conductive paste as an evaluation sample is measured with a rheometer at a rate of temperature increase of 3° C./min and it has not been possible even to suppress void formation.

As described above, in such thermal compression bonding technique, underfill has to have composition that exhibit viscosity behavior to manage both suppression of void formation and solder connection. However, in the current state, there is no manner to measure viscosity behavior of the underfill following the temperature behavior during the mounting step. Therefore, and it was not possible to predict viscosity behavior of the underfill with an arbitrary rate of temperature increase.

The present invention has been made in view of the above problems. It is an object of the present invention to provide a method of predicting viscosity behavior of a thermosetting resin, simulation software, a method of producing a thermosetting resin, and underfill produced in the production method in which viscosity behavior of a thermosetting resin, when a thermal compression bonding technique is carried out, may be predicted, and void generation in the underfill is suppressed while good solder connection is obtained.

(1) In order to achieve the above object, a method of predicting viscosity behavior of a thermosetting resin of the present invention is a method of predicting viscosity behavior of a thermosetting resin to predict viscosity behavior of the thermosetting resin with an arbitrary rate of temperature increase, the method including:

preparing a thermosetting resin as an evaluation sample;

measuring a reaction rate to measure a calorimetry peak of the thermosetting resin with three or more rates of temperature increase respectively;

measuring viscosity behavior to measure viscosity behavior of the thermosetting resin with the three or more rates of temperature increase respectively;

fitting a reaction rate to fit measurement data with each of the rates of temperature increase obtained by the measuring a reaction rate to a Kamal model formula, to obtain a fitting curve of calorimetry and time and a fitting curve of the calorimetry and a temperature of the thermosetting resin for each of the rates of temperature increase, and to calculate parameters in the Kamal model formula determined for a material of the thermosetting resin;

fitting viscosity behavior to fit the parameters in the Kamal model formula calculated in the fitting a reaction rate and the measurement data for each of the rates of temperature increase obtained by the measuring viscosity behavior to a Castro-Macosko model formula, to obtain fitting a curve of viscosity and time and a fitting curve of viscosity and a temperature of the thermosetting resin for each of the rates of temperature increase, and to calculate a parameter in the Castro-Macosko model formula determined by the material of the thermosetting resin; and calculating virtual viscosity behavior to calculate virtual viscosity behavior of the thermosetting resin at the arbitrary rate of temperature increase by simulation based on each fitting curve for each of the rates of temperature increase obtained by the fitting viscosity behavior.

(2) In the method of predicting viscosity behavior of a thermosetting resin of above (1), it is preferred that, in the measuring a reaction rate, the calorimetry peak of the thermosetting resin is measured with a differential scanning calorimetry measuring device.

(3) In the method of predicting viscosity behavior of a thermosetting resin of above (1) or (2), it is preferred that, in the measuring viscosity behavior, the viscosity behavior of the thermosetting resin is measured with a viscoelasticity measuring device.

(4) In the method of predicting viscosity behavior of a thermosetting resin of any one of above (1) to (3), it is preferred that the Kamal model formula used in the fitting a reaction rate is a modified Kamal model formula of an equation (B) below in which a Kamal model formula of an equation (A) below is imposed doubly.

$$\frac{\Delta \alpha(T)}{\Delta t} = \left(A_1 \exp\left(-\frac{E_1}{T+273.15}\right) + A_2 \exp\left(-\frac{E_2}{T+273.15}\right)\alpha(t)^m\right)(1-\alpha(t))^n \quad (A)$$

In the equation (A), $A_1$, $E_1$, $A_2$, $E_2$, m, and n are parameters determined for each material of the thermosetting resin.

$$\frac{d\alpha(t)}{dt} = \left(A_1 \exp\left(-\frac{E_1}{T(t)}\right) + A_2 \exp\left(-\frac{E_2}{T(t)}\right)\alpha(t)^m\right)(1-\alpha(t))^n \times \\ \frac{1}{1+\exp[T(t)-T_b]} + \left(B_1 \exp\left(-\frac{F_1}{T(t)}\right) + B_2 \exp\left(-\frac{F_2}{T(t)}\right)\alpha(t)^p\right) \\ (1-\alpha(t))^q \times \frac{1}{1+\exp[-T(t)-T_b]} \quad (B)$$

In the equation (B), $A_1$, $E_1$, $A_2$, $E_2$, m, n, $B_1$, $F_1$, $B_2$, $F_2$, p, q, and $T_b$ are parameters determined for each material of the thermosetting resin.

(5) It is preferred that, in the method of predicting viscosity behavior of a thermosetting resin of any one of above (1) to (4), the three or more rates of temperature increase are at least three rates of 2° C./min, 5° C./min, and 10° C./min.

(6) In order to achieve the above object, a method of producing a thermosetting resin of the present invention, includes: predicting the viscosity behavior of the thermosetting resin at the arbitrary rate of temperature increase in the method of predicting viscosity behavior of a thermosetting resin according to any one of above (1) to (5); and determining composition thereof.

(7) In order to achieve the above object, underfill of the present invention is underfill including the viscosity behavior at the arbitrary rate of temperature increase predicted in the method of producing a thermosetting resin according to above (6) and the composition thereof determined in the method, wherein the underfill is applied on a substrate before mounting an electronic component and is used for thermal compression bonding of compression bond for the electronic component on the substrate via the underfill, and the underfill has viscosity behavior to start viscosity increase of the underfill after starting melt of solder to connect the electronic component when the thermal compression bonding is performed at a predetermined rate of temperature increase.

(8) It is preferred that, in the underfill of above (7), the underfill has viscosity behavior in which the viscosity increase at a rate of temperature increase of approximately 3000° C./min starts between approximately 150 and 260° C.

According to the method of predicting viscosity behavior of a thermosetting resin, the simulation software, the method of producing a thermosetting resin, and the underfill produced in the production method of the present invention, viscosity behavior of a thermosetting resin, when a thermal compression bonding technique is carried out, may be predicted, and void generation in the underfill is suppressed while good solder connection is obtained.

BRIEF DESCRIPTION OF THE DRAWINGS

FIG. 5 is a flowchart illustrating a procedure of a step of measuring viscosity behavior in the method of predicting viscosity behavior of a thermosetting resin.

FIG. 6A is a graph illustrating a measurement result in the step of measuring a reaction rate and FIG. 6B is a table illustrating a gross calorific value for each rate of temperature increase.

FIG. 9A is a graph illustrating measured data of calorimetry and time of the thermosetting resin obtained by the step of measuring a reaction rate and a fitting curve obtained by the step of fitting a reaction rate. FIG. 9B is a graph illustrating measured data of calorimetry and temperatures of the thermosetting resin obtained by the step of measuring a reaction rate and a fitting curve obtained by the step of fitting a reaction rate.

FIG. 10 is a listing table illustrating parameters in a modified Kamal model formula calculated by a result of the step of fitting a reaction rate.

FIG. 11A is a graph illustrating measured data of viscosity of the thermosetting resin and time obtained by the step of measuring viscosity behavior and a fitting curve obtained by the step of fitting viscosity behavior. FIG. 11B is a graph illustrating measured data of viscosity of the thermosetting resin and temperatures obtained by the step of measuring viscosity behavior and a fitting curve obtained by the step of fitting viscosity behavior.

FIG. 12 is a listing table illustrating parameters in a Castro-Macosko model formula calculated by a result of the step of fitting a reaction rate.

FIG. 15A is a graph illustrating measured data of relationship between viscosity and time, and a fitting curve of predicted virtual viscosity behavior. FIG. 15B is a graph illustrating measured data of relationship between viscosity and temperatures, and a fitting curve of predicted virtual viscosity behavior.

DETAILED DESCRIPTION OF THE INVENTION

Descriptions are given below to a method of predicting viscosity behavior of a thermosetting resin, simulation software, a method of producing a thermosetting resin, and underfill produced in the production method according to one embodiment of the present invention with reference to the drawings.

<Device Configuration>

Figure 1:
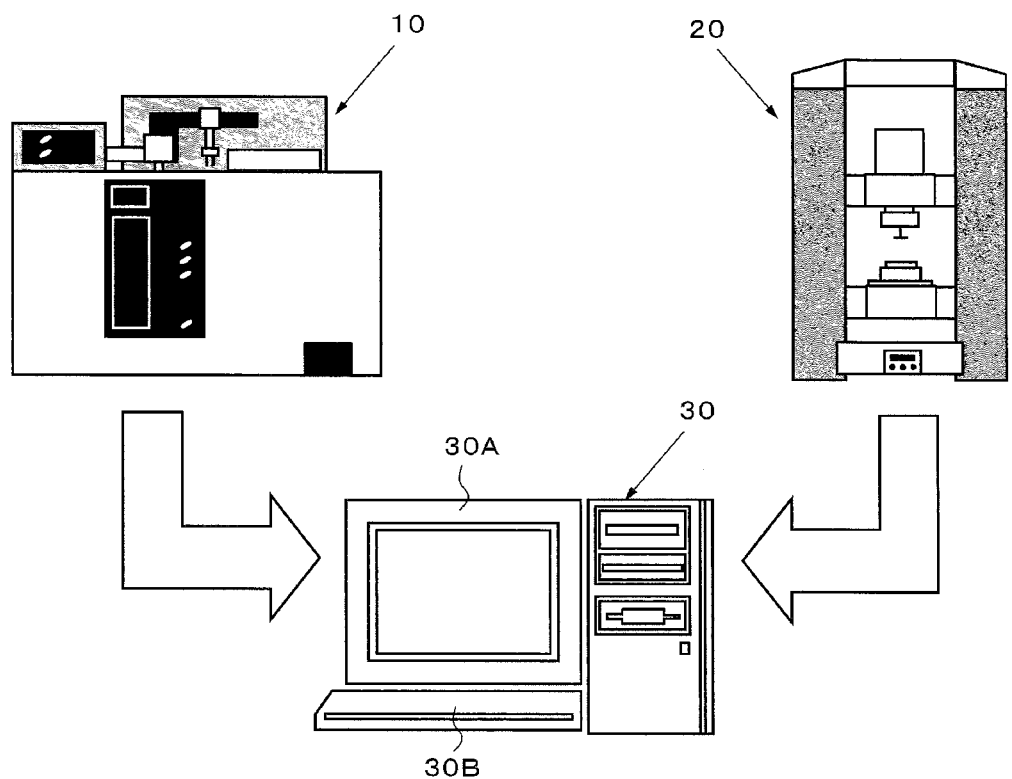
FIG. 1 is a schematic view illustrating a device to perform a method of predicting viscosity behavior of a thermosetting resin according to one embodiment of the present invention.
Figure 2:
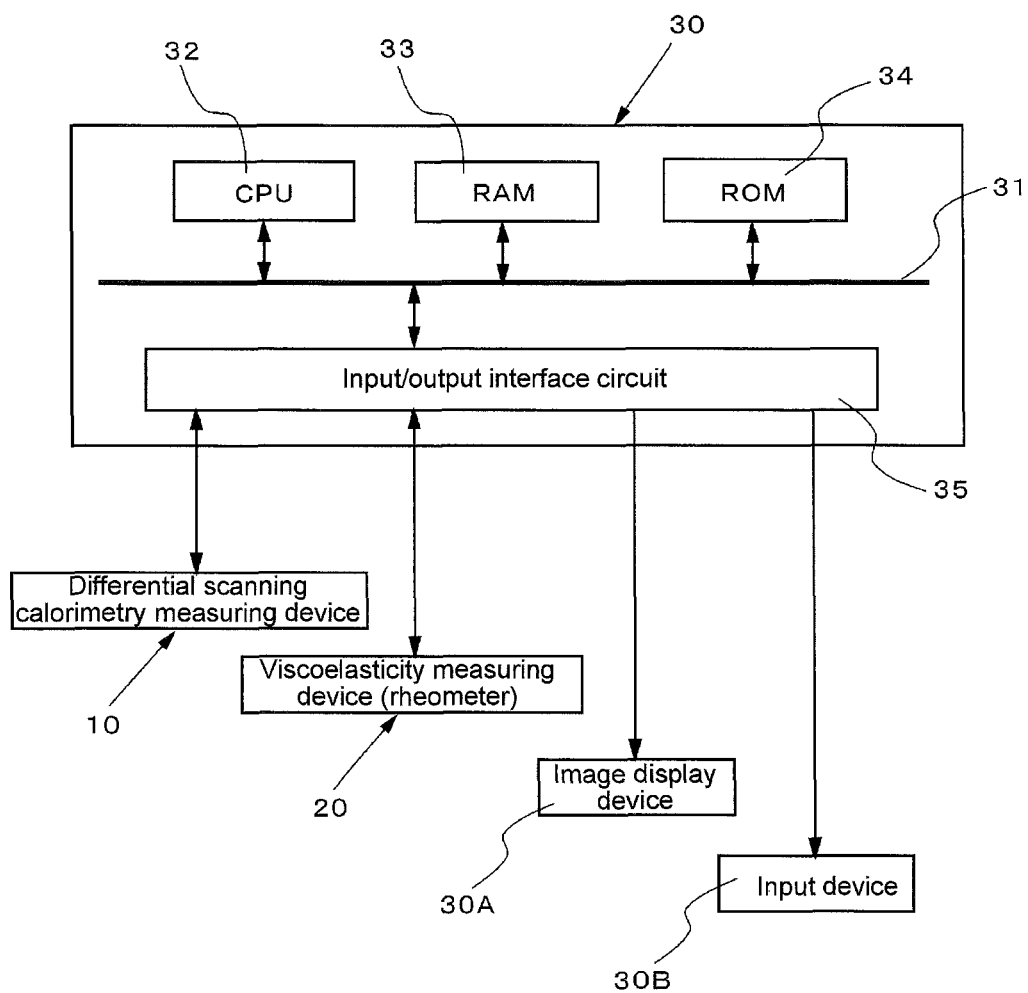
FIG. 2 is a block diagram illustrating configuration of the above device.

Firstly, descriptions are given to a device to perform a method of predicting viscosity behavior of a thermosetting resin according to the present embodiment with reference to FIGS. 1 and 2.

In the method of predicting viscosity behavior of a thermosetting resin according to the present embodiment, a reaction rate and viscosity behavior are actually measured with three rates of temperature increase regarding a thermosetting resin as an evaluation sample. Then, the measurement result is analyzed with dedicated simulation software according to the present embodiment, thereby generating a fitting curve related to viscosity behavior for each rate of temperature increase of the thermosetting resin. Based on these fitting curves related to the viscosity behavior, viscosity behavior of the thermosetting resin with an arbitrary rate of temperature increase is predicted.

In FIG. 1, the reference numeral 10 denotes a differential scanning calorimetry (DSC) measuring device to measure a reaction rate of the thermosetting resin with three rates of temperature increase. The differential scanning calorimetry measuring device 10 measures a temperature dependent calorimetry peak of the thermosetting resin with three rates of temperature increase. It is possible to use, for example, "DSC204F1 Phoenix®" manufactured by NETZSCH as the differential scanning calorimetry measuring device 10.

The reference numeral 20 denotes a rheometer (viscoelasticity measuring device) to measure viscosity behavior of the thermosetting resin with three rates of temperature increase. The rheometer 20 measures temperature dependent viscosity behavior of the thermosetting resin with three rates of temperature increase. It is possible to use, for example, "HAAKE MARSIII™" manufactured by Thermo SCIENTIFIC, as the rheometer 20.

Respective measurement data of the differential scanning calorimetry measuring device 10 and the rheometer 20 is inputted into a computer 30, and analyzed with simulation software of the present embodiment that is installed in the computer 30. As illustrated in FIG. 2, the computer 30 is provided with a CPU (central processing unit) 32, a RAM (a random access memory) 33, a ROM (a read only memory) 34, and an input/output interface circuit 35, which are connected to an input/output bus 31.

An image display device 30A such as a liquid crystal display and an input device 30B such as a keyboard and a mouse, as well as the differential scanning calorimetry measuring device 10 and the rheometer 20, are connected to the input/output interface circuit 35 of the computer 30. In the RAM 33, simulation software of the present embodiment is recorded as erasable record, and the simulation software is executed by the CPU 32.

A user sets measurement conditions of the differential scanning calorimetry measuring device 10 and the rheometer 20 through the computer 30, and the differential scanning calorimetry measuring device 10 and the rheometer 20 actually measure a reaction rate and viscosity behavior of the thermosetting resin with the measurement conditions. Measurement results of the differential scanning calorimetry measuring device 10 and the rheometer 20 are inputted into the computer 30 via the input/output interface circuit 35, and a result of analysis process by the computer 30 in accordance with the present simulation software is outputted to the image display device 30A.

Although the present embodiment is configured to download the present simulation software afterwards to the RAM 33 of the general purpose computer 30, the configuration is not limited to it. The simulation software of the present embodiment may also be recorded in the ROM 34 to make the computer 30 as a dedicated machine for the method of predicting viscosity behavior in the present embodiment.

<Simulation Software>

Figure 3:
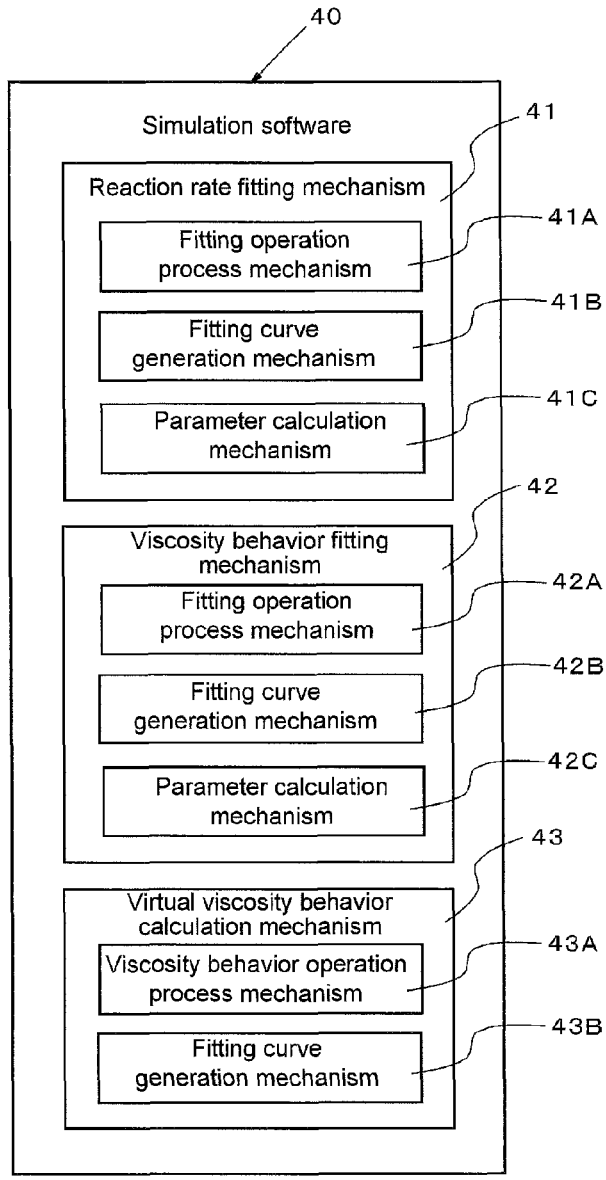
FIG. 3 is a functional block diagram illustrating configuration of simulation software to perform the method of predicting viscosity behavior of a thermosetting resin.

Next, descriptions are given to configuration of simulation software in the present embodiment that is recorded in the RAM 33 of the computer 30 with reference to FIG. 3.

In FIG. 3, simulation software 40 of the present embodiment is configured to mainly include a reaction rate fitting mechanism 41, a viscosity behavior fitting mechanism 42, and a virtual viscosity behavior calculation mechanism 43.

<<Reaction Rate Fitting Mechanism>>

The reaction rate fitting mechanism 41 is configured to include a fitting operation process mechanism 41A, a fitting curve generation mechanism 41B, and a parameter calculation mechanism 41C. The fitting operation process mechanism 41A carries out operation process to fit measurement data of each rate of temperature increase from the differential scanning calorimetry measuring device 10 illustrated in FIG. 1 to a Kamal model formula. The fitting curve generation mechanism 41B generates a fitting curve of calorimetry and time of the thermosetting resin and a fitting curve of the calorimetry and temperatures of the thermosetting resin for each rate of temperature increase based on a result of the operation process of the fitting operation process mechanism 41A. The parameter calculation mechanism 41C calculates parameters in a Kamal model formula determined by a material of the thermosetting resin.

<<Viscosity Behavior Fitting Mechanism>>

The viscosity behavior fitting mechanism 42 is configured to include a fitting operation process mechanism 42A, a fitting curve generation mechanism 42B, and a parameter calculation mechanism 42C. The fitting operation process mechanism 42A carries out operation process to fit the parameters in a Kamal model formula calculated by the reaction rate fitting mechanism 41 and the measurement data for each rate of temperature increase from the rheometer 20 illustrated in FIG. 1 to a Castro-Macosko model formula. The fitting curve generation mechanism 42B generates a fitting curve of viscosity and time of the thermosetting resin and a fitting curve of the viscosity and temperatures of the thermosetting resin for each rate of temperature increase based on a result of the operation process of the fitting operation process mechanism 42A. The parameter calculation mechanism 42C calculates parameters in a Castro-Macosko model formula determined by a material of the thermosetting resin.

<<Virtual Viscosity Behavior Calculation Mechanism>>

The virtual viscosity behavior calculation mechanism 43 is configured to include a viscosity behavior operation process mechanism 43A and a fitting curve generation mechanism 43B. The viscosity behavior operation process mechanism 43A calculates virtual viscosity behavior of the thermosetting resin with an arbitrary rate of temperature increase other than the three rates of temperature increase, based on the fitting curve of viscosity and time and the fitting curve of the viscosity and temperatures of the thermosetting resin generated by the viscosity behavior fitting mechanism 42 by simulation. The fitting curve generation mechanism 43B generates a fitting curve illustrating the virtual viscosity behavior of the thermosetting resin with an arbitrary rate of temperature increase based on a calculation result of the viscosity behavior operation process mechanism 43A.

<<Others>>

Figure 7:
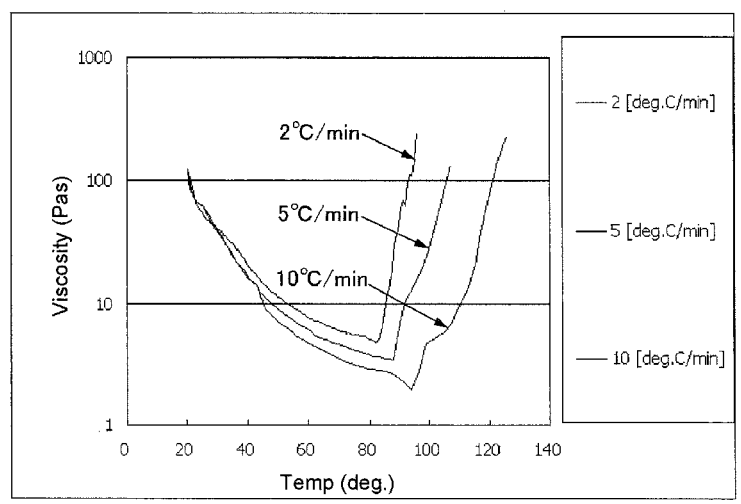
FIG. 7 is a graph illustrating a measurement result in the step of measuring viscosity behavior.

Although dedicated measurement and analysis software is generally prepared for the differential scanning calorimetry measuring device 10 and the rheometer 20, the simulation software 40 of the present embodiment may also include a program that analyzes measurement data of the differential scanning calorimetry measuring device 10 and the rheometer 20 to cause the computer 30 to generate a measurement result as illustrated in FIGS. 6A and 7.

<Method of Predicting Viscosity Behavior of Thermosetting Resin>

Next, detailed descriptions are given to a method of predicting viscosity behavior of a thermosetting resin in the present embodiment using the differential scanning calorimetry measuring device 10, the rheometer 20, and the computer 30 with reference to FIGS. 4 to 14.

<<Technical Significance of Present Measurement Method>>

In general, a thermal compression bonding technique is carried out at a fast temperature increase of 1800 to 3000° C./min, and there is a problem that voids occur depending on viscosity behavior of the underfill (thermosetting resin) to be used and connection failure of soldering occurs. That is, it is possible to suppress void generation when viscosity of the underfill to be used is high relative to the fast temperature increase of 1800 to 3000° C./min, which is liable to cause connection failure of soldering. On the contrary, connection failure of soldering does not occur when viscosity of the underfill to be used is low relative to the fast temperature increase of 1800 to 3000° C./min, which is liable to generate voids.

Although viscosity control during a fast temperature increase is required for development of underfill to be used in the thermal compression bonding technique, the rate of temperature increase in the thermal compression bonding technique, which is 1800 to 3000° C./min, is too high. On the other hand, a conventional general viscosity measuring device has limitation of measurement with a rate of temperature increase of 10° C./min, and it is not at all possible to measure actually the viscosity at the rate of temperature increase of 1800 to 3000° C./min with a conventional general viscosity measuring device. Further, since the viscosity of the underfill also rises due to start of gelation when the temperature increases, it is extremely difficult to predict viscosity of the underfill during a fast temperature increase of 1800 to 3000° C./min from the behavior during a slow temperature increase such as 10° C./min.

In a method of predicting viscosity behavior of a thermosetting resin of the present embodiment, viscosity prediction is carried out with taking the underfill cure during the fast temperature increase into account. In order to obtain dependency on the degree of cure of the underfill, the result of measurement for each of the three rates of temperature increase with the differential scanning calorimetry measuring device 10 is fit to the Kamal model formula. Subsequently, in order to obtain dependency on the rate of temperature increase of the underfill, the result of measurement for each of the three rates of temperature increase with the rheometer 20 is fit to the Castro-Macosko model formula. After that, the degree of cure and the rate of temperature increase of the underfill are combined to enable prediction of the viscosity behavior by integrating such behavior and taking it into account.

<<Step of Measuring Reaction Rate>>

Figure 4:
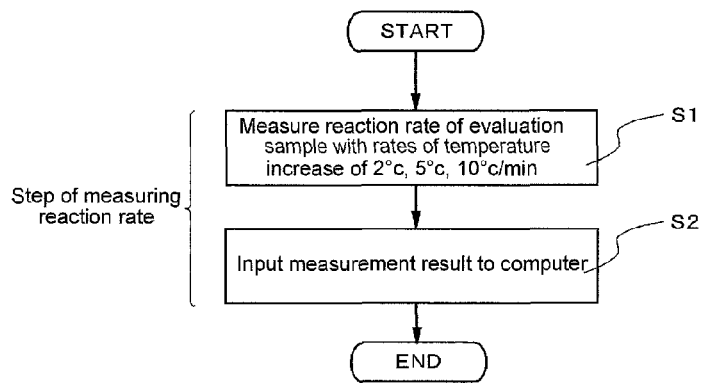
FIG. 4 is a flowchart illustrating a procedure of a step of measuring a reaction rate in the method of predicting viscosity behavior of a thermosetting resin.

FIG. 4 is a flowchart illustrating a procedure of a step of measuring a reaction rate of a thermosetting resin as an evaluation sample. In the step of measuring a reaction rate, with three or more rates of temperature increase, reaction rates of the thermosetting resin are measured respectively. In the present embodiment, calorimetry peaks of the thermosetting resin are measured respectively with the differential scanning calorimetry measuring device 10 illustrated in FIG. 1 with three rates of temperature increase of 2° C./min, 5° C./min, and 10° C./min using a preapplied underfill material "XS8448-196" manufactured by NAMICS Corporation, which is the present applicant, for the thermosetting resin (step S1 in FIG. 4).

The respective measurement data with three rates of temperature increase with the differential scanning calorimetry measuring device 10 is inputted into the computer 30, respectively (step S2 in FIG. 4). The computer 30 corrects a 0 (zero) value of the respective measurement data in accordance with software dedicated to the differential scanning calorimetry measuring device 10 or the simulation software in the present embodiment to generate a graph representing relationship between calorimetry and temperatures (temperature dependent reaction rate) as illustrated in FIG. 6A. According to the measurement result in FIG. 6A, it is understood that, in a case of any rate of temperature increase of 2° C./min, 5° C./min, and 10° C./min, although a small initial peak is exhibited, general reaction rate curves are plotted in which the peak temperature becomes higher as the rate of temperature increase becomes higher.

Here, the significance of measuring respective reaction rates of the thermosetting resin with three or more rates of temperature increase is to identify relationship between a variable amount and viscosity change when both are variable, in order to obtain a single formula considering the dependency on temperature and the dependency on rate of temperature increase of the viscosity of the thermosetting resin. Although it is expected that the identification accuracy increases with more measurement data with different rates of temperature increase, such as four rates, five rates, and six rates, an expected identification formula is obtained more actually. However, an expected identification formula can be obtained by measurement data with three rates of temperature increase.

In addition, regarding the significance of measuring a calorimetry peak of the thermosetting resin, viscosity of the thermosetting resin increases because a curing phenomenon occurs in which a reaction group of the resin opens the ring and starts reacting with a curing agent by giving a temperature and time. The calorimetry peak of the thermosetting resin suggests the temperature and the time at which the curing phenomenon precedes most. Accordingly, it is possible to reveal relationship between temperatures, time, and viscosity from the calorimetry peak of the thermosetting resin to learn viscosity change due to curing.

<<Step of Measuring Viscosity Behavior>>

FIG. 5 is a flowchart illustrating a procedure of a step of measuring viscosity behavior of the thermosetting resin. In the step of measuring viscosity behavior, with three rates of temperature increase of 2° C./min, 5° C./min, and 10° C./min, respective viscosity behavior of the thermosetting resin is measured with the rheometer 20 illustrated in FIG. 1 (step S11 in FIG. 5). The measurement is carried out in which the thermosetting resin is in a state of resin paste and the rheometer 20 has conditions of distortion of 0.5% and 1 Hz, using a parallel cone of 40 mm diameter with a gap of 500 μm.

The respective measurement data of the three types of viscosity behavior with the rheometer 20 is inputted respectively into the computer 30 (step S12 in FIG. 5). The computer 30 generates a graph representing relationship between viscosity and temperatures (temperature dependent viscosity) as illustrated in FIG. 7 in accordance with software dedicated to the rheometer 20 or a program of simulation software in the present embodiment.

<<Step of Fitting Reaction Rate>>

Figure 8:
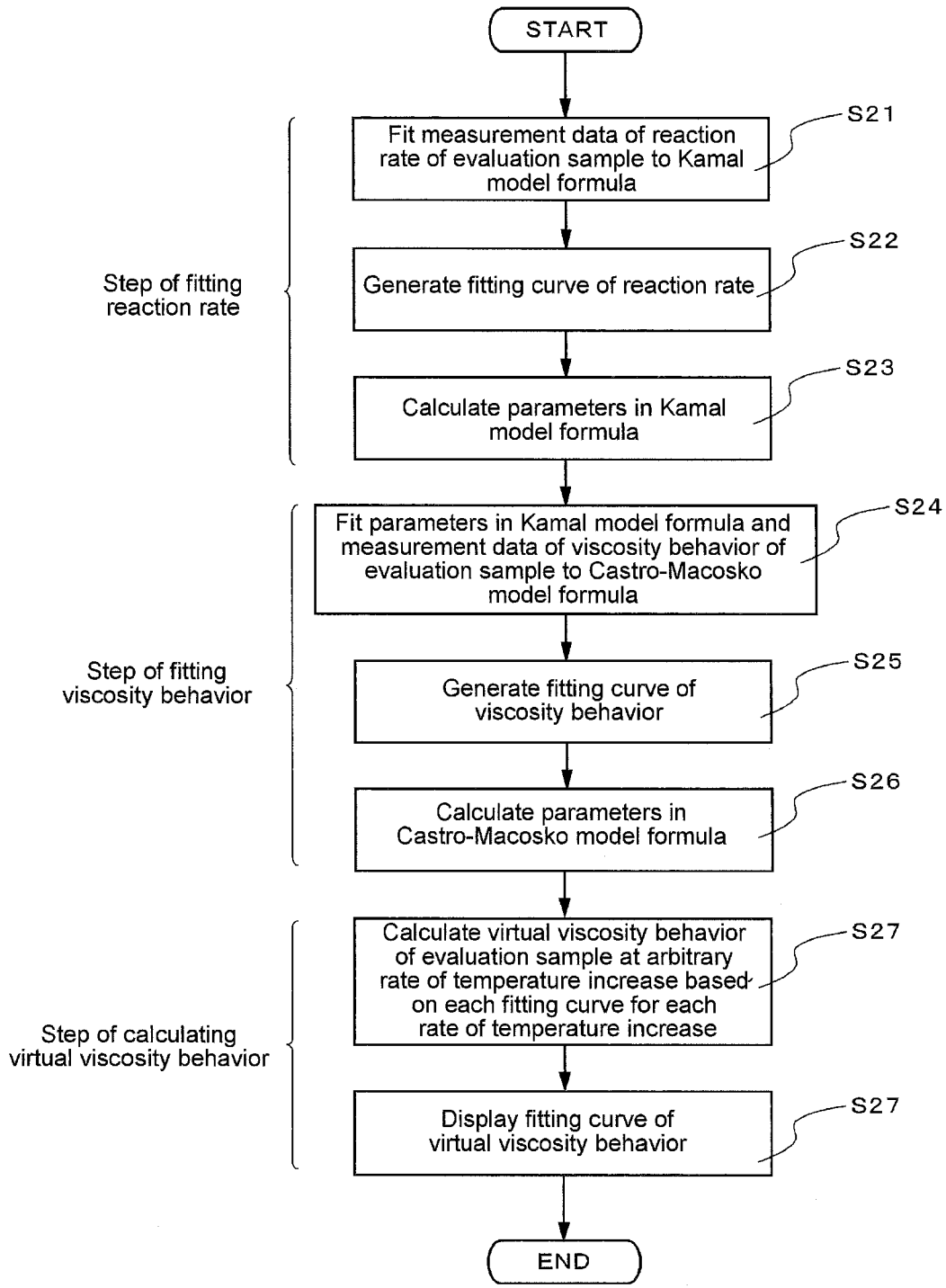
FIG. 8 is a flowchart illustrating a procedure of a step of fitting a reaction rate, a step of fitting viscosity behavior, and a step of calculating virtual viscosity behavior in the method of predicting viscosity behavior of a thermosetting resin.

FIG. 8 is a flowchart illustrating a procedure of a step of fitting a reaction rate, a step of fitting viscosity behavior, and a step of calculating virtual viscosity behavior in the method of predicting viscosity behavior of a thermosetting resin. Any of these steps is processed by the computer 30 based on measurement data in the step of measuring a reaction rate and the step of measuring viscosity behavior in accordance with a program of simulation software in the present embodiment.

Steps S21 to S23 in FIG. 8 show a procedure of the step of fitting a reaction rate. As preprocessing of steps S21 to S23, the computer 30 performs zero line correction of the measurement data obtained by the step of measuring a reaction rate in FIG. 4, to adjust data with difference as small as possible in the gross calorific value for each rate of temperature increase. When difference occurs in the gross calorific value for each rate of temperature increase, there is an uncured portion in the thermosetting resin, so that a decrease in precision is predicted.

Subsequently, the process goes on to step S21, and the computer 30 fits the measurement data for each rate of temperature increase obtained by the step of measuring a reaction rate in FIG. 4 to a Kamal model formula of an equation (1) below. The Kamal model formula is a formula for modelled curve of a reaction rate curve that is relationship between calorimetry and temperatures of a thermosetting resin measured in conditions with a constant rate of temperature increase and constant mass (in terms of per unit mass).

$$\frac{\Delta\alpha(T)}{\Delta t} = \left(A_1\exp\left(-\frac{E_1}{T+273.15}\right) + A_2\exp\left(-\frac{E_2}{T+273.15}\right)\alpha(t)^m\right)(1-\alpha(t))^n \quad (1)$$

In the equation (1), $A_1$, $E_1$, $A_2$, $E_2$, m, and n are parameters determined for each material of the thermosetting resin.

In the Kamal model equation, α is degree of cure, dα/dt (or $\Delta\alpha(T)/\Delta t$) is cure rate, T is temperature. $A_1$, $A_2$, $E_1$, $E_2$, m and n are the parameters that depend on curing reaction, which means that they are determined for each material.

The units of $A_1$ and $A_2$ are 1/time (1/sec), $E_1$ and $E_2$ are absolute temperature (K), m and n are dimensionless numbers.

Here, although the present inventors have initially fit measurement data in the step of measuring a reaction rate using the equation (1), it was not possible to keep the measurement data within a margin of convergence error for the equation (1) and it was diverged. It may be because there was difference in the gross calorific value for each rate of temperature increase. FIG. 6B illustrates the gross calorific value for each rate of temperature increase. As illustrated in FIG. 6B, it is understood that there is variation of approximately 8% to 5% in the gross calorific value for each rate of temperature increase.

Considering facts above, fitting by a modified Kamal model formula of an equation (2) below, in which the Kamal model formula of the equation (1) was doubly, was attempted in the present embodiment, for dealing with a case that there is variation in the gross calorific value for each rate of temperature increase, a case that there are a plurality of calorimetry peaks and many noises, and the like.

$$\frac{d\alpha(t)}{dt} = \left(A_1\exp\left(-\frac{E_1}{T(t)}\right) + A_2\exp\left(-\frac{E_2}{T(t)}\right)\alpha(t)^m\right)(1-\alpha(t))^n \times \quad (2)$$
$$\frac{1}{1+\exp[T(t)-T_b]} + \left(B_1\exp\left(-\frac{F_1}{T(t)}\right) + B_2\exp\left(-\frac{F_2}{T(t)}\right)\alpha(t)^p\right)$$
$$(1-\alpha(t))^q \times \frac{1}{1+\exp[-T(t)-T_b]}$$

In the equation (2), $A_1$, $E_1$, $A_2$, $E_2$, m, n, $B_1$, $F_1$, $B_2$, $F_2$, p, q, and $T_b$ are parameters determined for each material of the thermosetting resin. The units of $A_1$, $A_2$, $B_1$ and $B_2$ are 1/time (1/sec), $E_1$, $E_2$, $F_1$ and $F_2$ are absolute temperature (K), m, n, p and q are dimensionless numbers.

The Kamal model formula of the equation (1) is to fit with six parameters while the modified Kamal model formula of the equation (2) in the present embodiment is to fit with twelve parameters, which is twice of that. As a result, it becomes possible to fit a complex model more flexibly.

The Kamal model can be used in order to determine the cure rate of a resin material. The Kamal model of an equation (1) and the modified Kamal model formula of an equation (2) are described. The Kamal model is demonstrated as an example. There are several unknown parameters ($A_1$, $A_2$, $E_1$, $E_2$, m and n) to be determined in the Kamal model equation. Measurement data by Differential Scanning calorimeter (DSC) is used for determining the parameters in the Kamal model equation. Temperature (T) and reaction rate (dα/dt) are obtained by DSC measurement. The Kamal model that fit the behavior of cure rate of a resin material precisely can be obtained by performing a simulation. In order to find out unknown parameters by the simulation, a target function is used.

Target function=Σ[(measured data)−(model equation)]²

(Σ is a total for all of all measurement data)

If parameter values that makes the value of the target function minimum by the simulation, the Kamal model equation with the parameter values should fit the measurement data precisely. In order to find out the parameter values, a computer simulation is performed. An example of a simulation for determining the parameter values A downhill simplex method is commonly used for obtaining minimum value of the target function as an optimization algorithm. The downhill simplex method uses the concept of a simplex, which is a special polytope of n+1 vertices in n dimensions. The downhill simplex method has a series of steps, most steps just moving the point of the simplex where the function is largest ("highest point") through the opposite face of the simplex to a lower point. These steps are called "reflection". Also other steps of "expansion", "contraction" and "reduction", as well as "reflection", are repeatedly performed in order to find out the minimum of a target function. The principal simplex method is found in the paper as follows.

J. A. Nelder and R. Mead, Computer Journal, Vol. 7, pp. 308-313 (1965)

A sample code (program) of an improved downhill simplex method with a source code is disclosed in the paper as follows.

Numerical Recipes in Fortran 77, The Art of Scientific Computing (1986), Chapter 10.4 "Downhill Simplex Method in Multidimensions", pp. 402

Simulations for the modified Kamal model formula of an equation (2) and Castro-Macosko model formula can be performed with a similar manner as the Kamal model described above. Please note that, measurement date of viscosity behavior is used for a simulation in order to determine unknown parameters in the Cross-Macosko model.

Subsequently, the process goes on to step S22 in FIG. 8, and the computer 30 generates a fitting curve of reaction rate for each rate of temperature increase. FIGS. 9A and 9B illustrate fitting curves of reaction rate for each rate of temperature increase generated by the modified Kamal model formula of the equation (2). FIG. 9A is a graph illustrating the measured data of calorimetry of the thermosetting resin and time (time dependent reaction rate) obtained by step S11 in FIG. 5 and the fitting curve obtained by step S22 in FIG. 8. FIG. 9B is a graph illustrating the measured data of calorimetry of the thermosetting resin and temperatures (temperature dependent reaction rate) obtained by step S11 in FIG. 5 and the fitting curve obtained by step S22 in FIG. 8.

As illustrated in FIGS. 9A and 9B, when comparing the measured data of reaction rate with the fitting curves, there are no problems in the fitting curves because the behaviors of the measured data and fitting curves in rise and decay are almost coincided with each other, even if there is some difference in calorific value near the peak.

Subsequently, the process goes on to step S23 in FIG. 8. In step S23, the computer 30 calculates the parameters $A_1$, $E_1$, $A_2$, $E_2$, m, n, $B_1$, $F_1$, $B_2$, $F_2$, p, q, and $T_b$ in the modified Kamal model formula of above (2) determined for the material of the thermosetting resin based on the fitting result steps S21 and S22. FIG. 10 illustrates a list of these parameters.

<<Step of Fitting Viscosity Behavior>>

Steps S24 to S26 in FIG. 8 show a procedure of the step of fitting viscosity behavior. Firstly, in step S24, the computer 30 fits the parameters in the modified Kamal model formula of the equation (2) calculated in step S23 and the measurement data for each rate of temperature increase obtained by the step of measuring viscosity behavior (steps S11 and S12) in FIG. 5 to a Castro-Macosko model formula of an equation (4) below. Here, the Castro-Macosko model formula of the equation (4) below is made by applying the Castro model formula to a thermoplastic part of a Macosko model formula of an equation (3) below. The Macosko model formula of the equation (3) below is a formula for modelled curve of a viscosity growth curve representing a relationship between time and the viscosity of a thermosetting resin measured with a condition of constant rate of temperature increase.

$$\eta(t) = \underbrace{\eta_{tp}(T, \dot{\gamma})}_{\text{Thermoplastic Properties}} \underbrace{\left(\frac{\alpha_{gel}}{\alpha_{gel} - \alpha(t)}\right)^{E+F\alpha(t)}}_{\text{Thermosetting Properties}} \quad (3)$$

$$\eta(t) = \frac{\eta_0(T)}{1 + \left(\frac{\eta_0(T)\omega}{\tau^*}\right)^{1-r}} \left(\frac{\alpha_{gel}}{\alpha_{gel} - \alpha(t)}\right)^{E+F\alpha(t)} \quad (4)$$

$$\eta_0(T) = B\exp\left(\frac{T_B}{T}\right)$$

In the equation (4), B, TB, $\tau^*$, r, ω, $\alpha_{gel}$, E, and F are parameters determined for each material of the thermosetting resin.

Subsequently, the process goes on to step S25 in FIG. 8, and the computer 30 generates a fitting curve of viscosity behavior for each rate of temperature increase. FIGS. 11A and 11B illustrate fitting curves of viscosity behavior for each rate of temperature increase generated by the Castro-Macosko model formula of the equation (4). FIG. 11A is a graph illustrating the measured data and time of calorimetry of the thermosetting resin (time dependent viscosity) obtained by step S1 in FIG. 4 and the fitting curves obtained by step S25 in FIG. 8. FIG. 11B is a graph illustrating the measured data of calorimetry and temperatures of the thermosetting resin (temperature dependent viscosity) obtained by step S1 in FIG. 4 and the fitting curves obtained by step S25 in FIG. 8. As illustrated in FIGS. 11A and 11B, when comparing the measured data of viscosity behavior with the fitting curves, there are no problems in the fitting curves because the behaviors of the measured data and fitting curves are almost coincided with each other.

Subsequently, the process goes on to step S26 in FIG. 8. In step S26, the computer 30 calculates the parameters B, TB, $\tau^*$, r, ω, $\alpha_{gel}$, E, and F in the Castro-Macosko model formula of the above (4) determined for the material of the thermosetting resin based on the fitting result in steps S24 and S25. FIG. 12 illustrates a list of these parameters.

<<Step of Calculating Virtual Viscosity Behavior>>

Steps S27 and S28 in FIG. 8 show a procedure of the step of calculating virtual viscosity behavior. In step S27, the computer 30 calculates virtual viscosity behavior of the thermosetting resin with an arbitrary rate of temperature increase based on each fitting curve for each rate of temperature increase obtained by steps S24 to S26 by simulation. After that, the process goes on to step S28, the computer 30 generates a fitting curve representing virtual viscosity behavior of the thermosetting resin with an arbitrary rate of temperature increase based on the calculation result in step S27.

Figure 13:
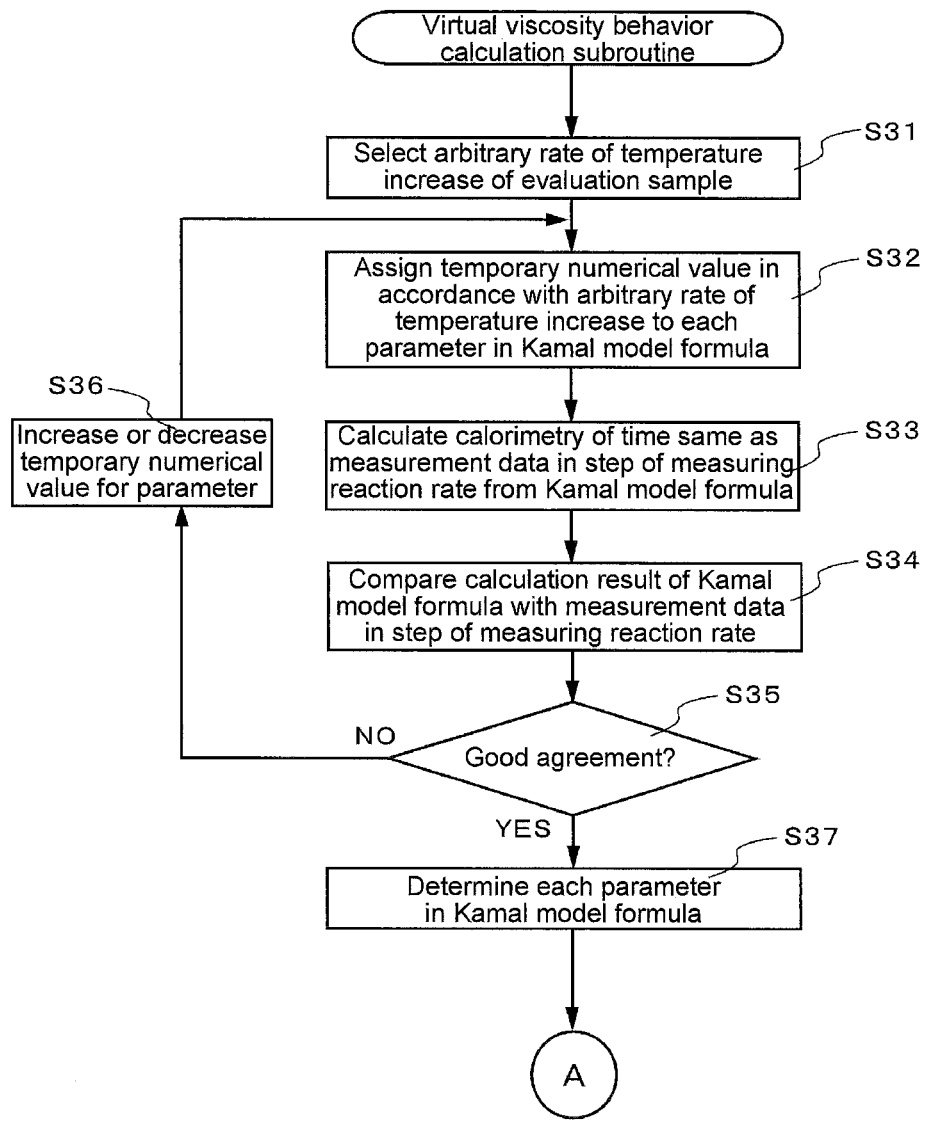
FIG. 13 is a flowchart of a first half (reaction rate part) of a virtual viscosity behavior calculation subroutine showing specific processes in the step of calculating virtual viscosity behavior.
Figure 14:
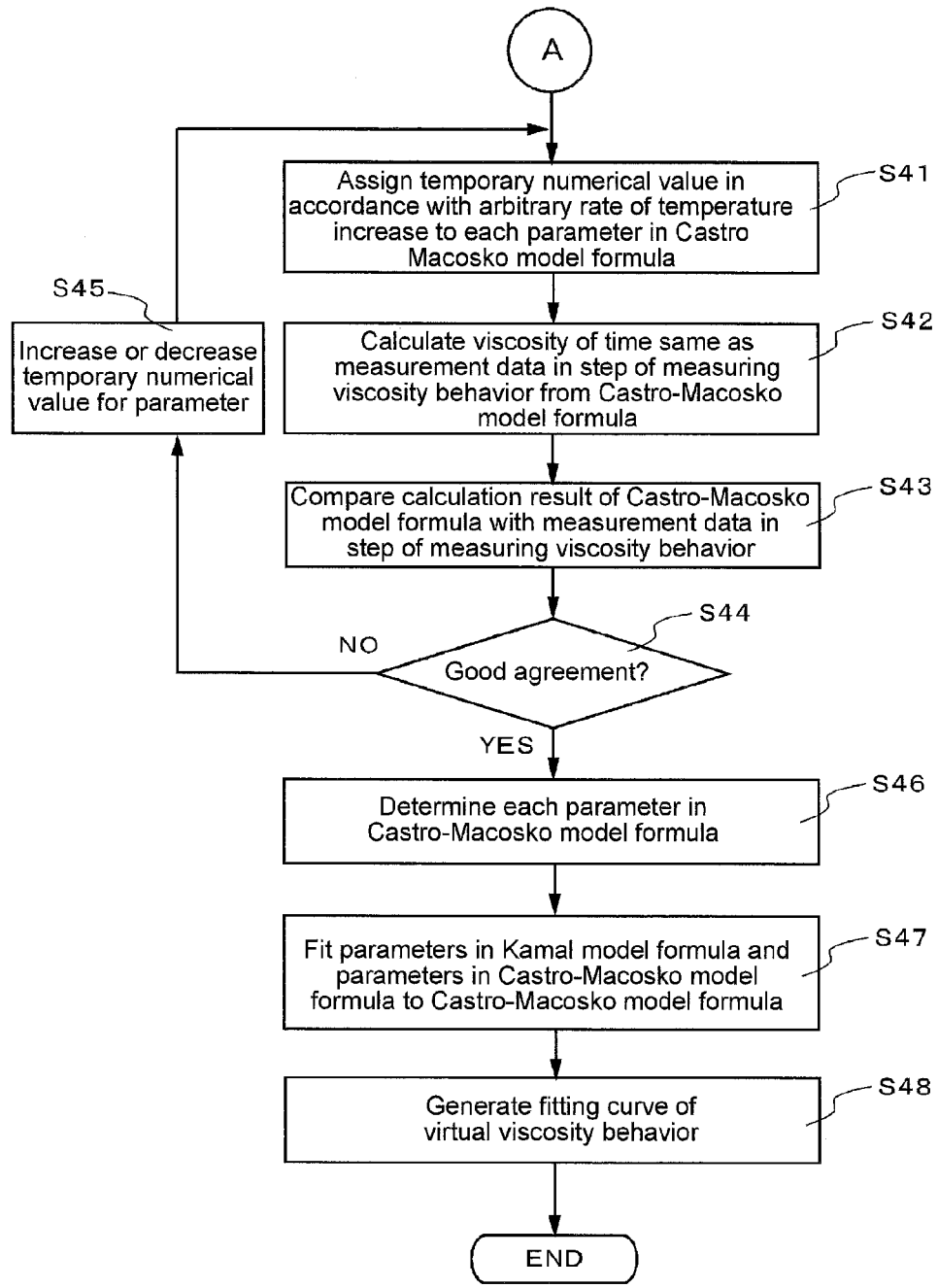
FIG. 14 is a flowchart of a last half (viscosity behavior part) of the same virtual viscosity behavior calculation subroutine.

Here, descriptions are given to the process of simulation carried out in step S27, which is the step of calculating virtual viscosity behavior, with reference to a virtual viscosity behavior calculation subroutine illustrated in FIGS. 13 and 14. FIG. 13 illustrates the first half of the process for a reaction rate part, and FIG. 14 illustrates the last half of the process for a viscosity behavior part.

Firstly, in step S31 in FIG. 13, the computer 30 selects an arbitrary rate of temperature increase for an evaluation sample in accordance with an input of a user. The "arbitrary rate of temperature increase" here may be a fast temperature increase of, for example, 1800 to 3000° C./min at which the rheometer 20 is not capable of measuring.

Subsequently, the process goes on to step S32, the computer 30 assigns a temporary numerical value in accordance with the arbitrary rate of temperature increase to each parameter in the Kamal model formula (the modified Kamal model formula in the present embodiment). Then, the process goes on to step S33, and the computer 30 calculates calorimetry for the time same as the step of measuring a reaction rate (step S1) in FIG. 4 from the Kamal model formula.

After that, in step S34, the computer 30 compares the calculation result of calorimetry from the Kamal model formula with the measurement data of calorimetry in the step of measuring a reaction rate (step S1) in FIG. 4 and determines whether or not agreement of these values is good (whether or not in an acceptable range). When determined that the agreement is not good (NO), the process goes on to step S36 and the computer 30 repeats the process in step S32 to S35 by increasing or decreasing the temporary numerical value to be assigned to each parameter in the Kamal model formula. On the other hand, when it is determined that the agreement is good (YES), the process goes on to step S37 and the computer 30 determines each parameter in the Kamal model formula.

Subsequently, the process goes on to step S41 in FIG. 14 and the computer 30 assigns a temporary numerical value in accordance with the arbitrary rate of temperature increase to each parameter in the Castro-Macosko model formula. Then, the process goes on to step S42 and the computer 30 calculates viscosity of the time same as the step of measuring viscosity behavior (step S11) in FIG. 5 from the Castro-Macosko model formula.

After that, in step S43, the computer 30 compares the calculation result of calorimetry from the Castro-Macosko model formula with the measurement data of viscosity in the step of measuring viscosity behavior (step S11) in FIG. 5 and determines whether or not agreement of these values is good (whether or not in an acceptable range). When determined that the agreement is not good (NO), the process goes on to step S45 and the computer 30 repeats the process in steps S41 to S44 by increasing or decreasing the temporary numerical value to be assigned to each parameter in the Castro-Macosko model formula. On the other hand, when determined that the agreement is good (YES), the process goes on to step S46 and the computer 30 determines each parameter in the Castro-Macosko model formula.

Subsequently, the process goes on to step S47 and the computer 30 fits each parameter in the Kamal model formula determined in step S37 in FIG. 13 and each parameter in the Castro-Macosko model formula determined in step S46 to the Castro-Macosko model formula and generates a fitting curve of virtual viscosity behavior (step S48). The fitting curve thus generated is displayed on the image display device 30A of the computer 30, for example, as in FIG. 16 described later (step S27 in FIG. 8).

<<<Verification of Reproducibility of Virtual Viscosity Behavior>>>

In the present embodiment, reproducibility of the virtual viscosity behavior calculated by the computer 30 is verified by setting the arbitrary rate of temperature increase at 3° C./min, at which the rheometer 20 is capable of measuring. That is, the computer 30 is caused to calculate virtual viscosity behavior of the thermosetting resin in a condition of a rate of temperature increase of 3° C./min based on each fitting curve for each rate of temperature increase obtained by steps S24 to S26, and in the meanwhile, viscosity behavior of the thermosetting resin is actually measured in a condition of a rate of temperature increase of 3° C./min using the rheometer 20 to compare the fitting curve of the predicted virtual viscosity behavior with the measured data.

Figure 15A:
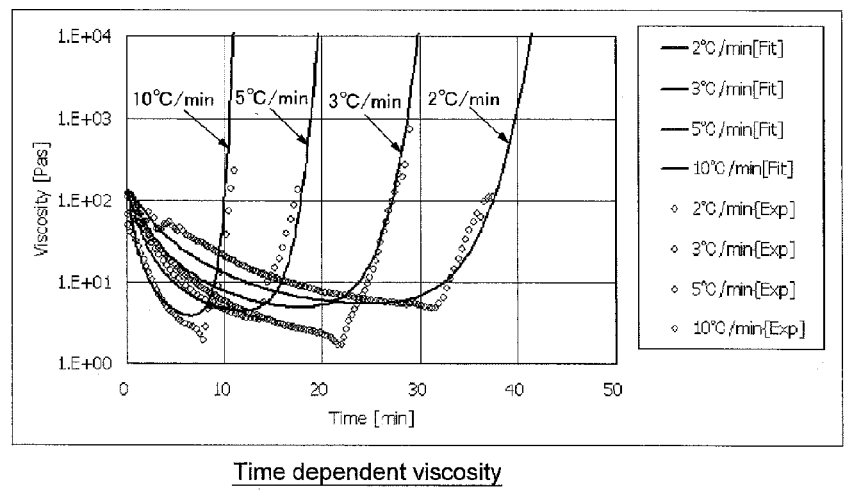
FIGS. 15A and 15B are comparison between a measured value and a fitting curve of predicted virtual viscosity behavior, by setting an arbitrary rate of temperature increase at 3° C. in the step of calculating virtual viscosity behavior.
Figure 15B:
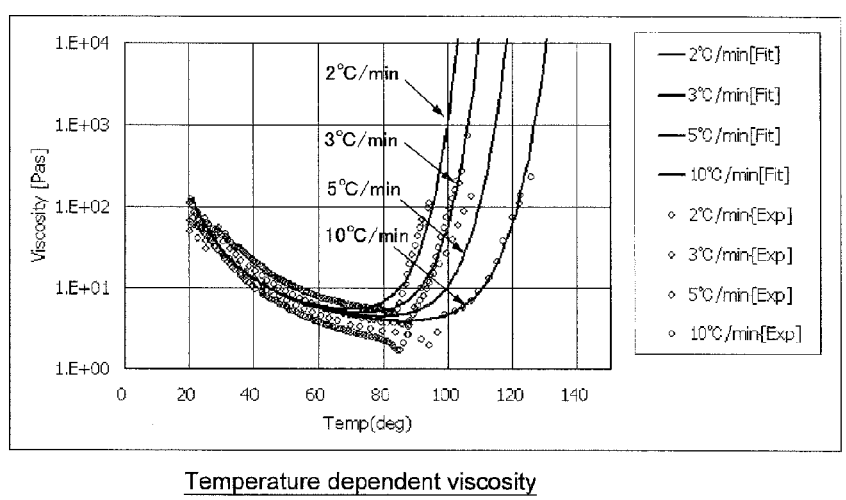

FIGS. 15A and 15B illustrate the comparison results. FIG. 15A is a graph illustrating the measured data of relationship between viscosity and time (time dependent viscosity) and the fitting curves of predicted virtual viscosity behavior, and FIG. 15B is a graph illustrating the measured data of relationship between viscosity and temperatures (temperature dependent viscosity) and the fitting curves of predicted virtual viscosity behavior. It is understood that, focusing on the measured data at a rate of temperature increase of 3° C./min and its fitting curve among these graphs, the fitting curve at a rate of temperature increase of 3° C./min calculated by the computer 30 almost coincides with the measured data.

<<<Application to Fast Temperature Increase>>>

In case, for example, mounting tact of 4 sec, which is a condition currently required for non-conductive paste used in the thermal compression bonding technique, the rate of temperature increase goes up to 260° C. with 1800° C./min (approximately 30° C./sec) while there is a problem that voids occur during the tact in the current situation. As a result of keen examination of the present inventors, it is considered to be advantageous for suppression of void formation that a resin is highly viscous around 220° C., which is the solder melting temperature, while there is no manner in measuring methods in the current situation other than guessing based on the measured data of temperature dependent viscosity, and it also used to be difficult to determine the viscosity.

Figure 16:
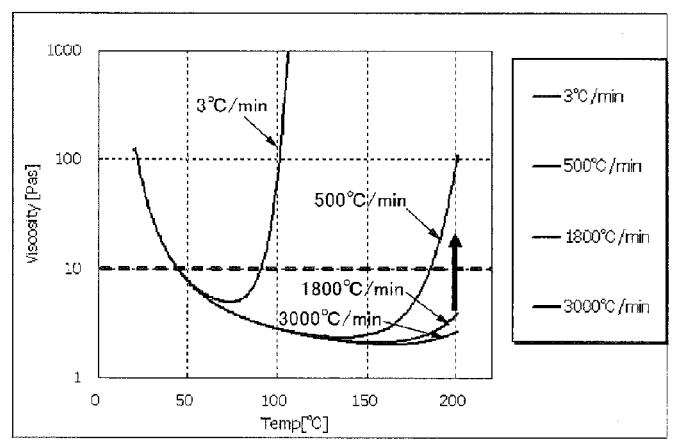
FIG. 16 is a graph illustrating, fitting curves to predict the virtual viscosity behavior, by setting the arbitrary rate of temperature increase at 3° C./min, 500° C./min, 1800° C./min, and 3000° C./min in the step of calculating virtual viscosity behavior.
Figure 17A:
FIGS. 17A to 17F are schematic views illustrating a series of steps in a capillary flow technique.
Figure 17B:
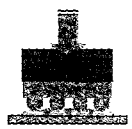
Figure 17C:
Figure 17D:
Figure 17E:
Figure 17F:
Figure 18A:
FIGS. 18A to 18C are schematic views illustrating a series of steps in a thermal compression bonding technique.
Figure 18B:
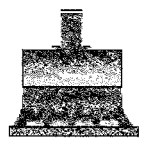
Figure 18C:

FIG. 16 illustrates a fitting curve of virtual viscosity behavior in which a rate of temperature increase of 1800° C./min, which is predicted in the method of predicting viscosity behavior of a thermosetting resin in the present embodiment. For comparison, prediction results of 3° C./min, 500° C./min, and 3000° C./min are also shown. According to the fitting curve of the virtual viscosity behavior in which the rate of temperature increase of 1800° C./min is predicted, while the viscosity rises from around 200° C., it is very low viscous without being thickened even around 200° C., which is considered that voids occur. Accordingly, for development of a thermosetting resin in which void generation is suppressed, a direction of improvement to increase the viscosity around 200° C. is suggested as illustrated with an arrow in FIG. 16.

In such a manner, according to the method of predicting viscosity behavior of a thermosetting resin according to the present embodiment, it is possible to greatly reduce the number of steps in development of a thermosetting resin as underfill, and it also becomes possible to expand improvement by considering mechanism of a thermosetting resin and development of a resin material having new advantages.

The invention claimed is:

1. A method of predicting viscosity behavior of a thermosetting resin to predict viscosity behavior of the thermosetting resin with an arbitrary rate of temperature increase, the method comprising:

preparing a thermosetting resin as an evaluation sample;

measuring a reaction rate to measure a calorimetry peak of the thermosetting resin with three or more rates of temperature increase respectively;

measuring viscosity behavior to measure viscosity behavior of the thermosetting resin with the three or more rates of temperature increase respectively;

fitting a reaction rate to fit measurement data with each of the rates of temperature increase obtained by the measuring a reaction rate to a Kamal model formula, to obtain a fitting curve of calorimetry and time and a fitting curve of the calorimetry and a temperature of the thermosetting resin for each of the rates of temperature increase, and to calculate parameters in the Kamal model formula determined for a material of the thermosetting resin;

fitting viscosity behavior to fit the parameters in the Kamal model formula calculated in the fitting a reaction rate and the measurement data for each of the rates of temperature increase obtained by the measuring viscosity behavior to a Castro-Macosko model formula, to obtain fitting a curve of viscosity and time and a fitting curve of viscosity and a temperature of the thermosetting resin for each of the rates of temperature increase, and to calculate a parameter in the Castro-Macosko model formula determined by the material of the thermosetting resin; and calculating virtual viscosity behavior to calculate virtual viscosity behavior of the thermosetting resin at the arbitrary rate of temperature increase by simulation based on each fitting curve for each of the rates of temperature increase obtained by the fitting viscosity behavior.

2. The method of predicting viscosity behavior of a thermosetting resin according to claim 1, wherein, in the measuring a reaction rate, the calorimetry peak of the thermosetting resin is measured with a differential scanning calorimetry measuring device.

3. The method of predicting viscosity behavior of a thermosetting resin according to claim 1, wherein, in the measuring viscosity behavior, the viscosity behavior of the thermosetting resin is measured with a viscoelasticity measuring device.

4. The method of predicting viscosity behavior of a thermosetting resin according to claim 1, wherein the Kamal model formula used in the fitting a reaction rate is a modified Kamal model formula of an equation (2) below in which a Kamal model formula of an equation (1) below is imposed doubly, $$\frac{\Delta \alpha(T)}{\Delta t} = \left(A_1 \exp\left(-\frac{E_1}{T+273.15}\right) + A_2 \exp\left(-\frac{E_2}{T+273.15}\right) \alpha(t)^m\right)(1-\alpha(t))^n \quad (1)$$

wherein $A_1$, $E_1$, $A_2$, $E_2$, m, and n are parameters determined for each material of the thermosetting resin and wherein the units of $A_1$ and $A_2$ are 1/time (1/sec), $E_1$ and $E_2$ are absolute temperature (K), m and n are dimensionless numbers, and $$\frac{d\alpha(t)}{dt} = \left(A_1 \exp\left(-\frac{E_1}{T(t)}\right) + A_2 \exp\left(-\frac{E_2}{T(t)}\right) \alpha(t)^m\right)(1-\alpha(t))^n \times \quad (2)$$
$$\frac{1}{1+\exp[T(t)-T_b]} + \left(B_1 \exp\left(-\frac{F_1}{T(t)}\right) + B_2 \exp\left(-\frac{F_2}{T(t)}\right) \alpha(t)^p\right)$$
$$(1-\alpha(t))^q \times \frac{1}{1+\exp[-T(t)-T_b]}$$

wherein $A_1$, $E_1$, $A_2$, $E_2$, m, n, $B_1$, $F_1$, $B_2$, $F_2$, p, q, and $T_b$ are parameters determined for each material of the thermosetting resin and wherein the units of $A_1$, $A_2$, $B_1$ and $B_2$ are 1/time (1/sec), $E_1$, $E_2$, $F_1$ and $F_2$ are absolute temperature (K), m, n, p and q are dimensionless numbers.

5. The method of predicting viscosity behavior of a thermosetting resin according to claim 1, wherein the three or more rates of temperature increase are at least three rates of 2° C./min, 5° C./min, and 10° C./min.

6. A method of producing a thermosetting resin, comprising:

predicting the viscosity behavior of the thermosetting resin at the arbitrary rate of temperature increase in the method of predicting viscosity behavior of a thermosetting resin according to claim 1; and determining composition of the thermosetting resin.

7. Underfill produced by the method according to claim 6, comprising the viscosity behavior at the arbitrary rate of temperature increase predicted in the method of producing a thermosetting resin and the determined composition, wherein the underfill is applied on a substrate before mounting an electronic component and is used for thermal compression bonding of compression bond for the electronic component on the substrate via the underfill, and the underfill has viscosity behavior to start viscosity increase of the underfill after starting melt of solder to connect the electronic component when the thermal compression bonding is performed at a predetermined rate of temperature increase.

8. The underfill according to claim 7, wherein the underfill has viscosity behavior in which the viscosity increase at a rate of temperature increase of approximately 3000° C./min starts between approximately 150 and 260° C.

* * * * *